United States Patent
Zhang et al.

(10) Patent No.: US 9,272,978 B2
(45) Date of Patent: Mar. 1, 2016

(54) HYDROXY ACID ESTER COMPOUND OF SUBSTITUTED PHENOL, PREPARATION METHOD AND MEDICAL USE THEREOF

(75) Inventors: Wensheng Zhang, Sichuan (CN); Jun Yang, Sichuan (CN); Jin Liu, Sichuan (CN)

(73) Assignee: West China Hospital, Sichuan University, Sichuan (CN)

( * ) Notice: Subject to any disclaimer, the term of this patent is extended or adjusted under 35 U.S.C. 154(b) by 457 days.

(21) Appl. No.: 13/702,188

(22) PCT Filed: Oct. 13, 2010

(86) PCT No.: PCT/CN2010/001600
§ 371 (c)(1),
(2), (4) Date: Dec. 5, 2012

(87) PCT Pub. No.: WO2011/160267
PCT Pub. Date: Dec. 29, 2011

(65) Prior Publication Data
US 2013/0079405 A1 Mar. 28, 2013

(30) Foreign Application Priority Data
Jun. 23, 2010 (CN) .......................... 2010 1 02069361

(51) Int. Cl.
*C07C 67/32* (2006.01)
*C07C 67/31* (2006.01)
*C07C 69/675* (2006.01)
*C07C 59/48* (2006.01)

(52) U.S. Cl.
CPC ................. *C07C 59/48* (2013.01); *C07C 67/31* (2013.01); *C07C 67/32* (2013.01); *C07C 69/675* (2013.01)

(58) Field of Classification Search
CPC .............................. C07C 67/08; C07C 67/31
See application file for complete search history.

(56) References Cited

U.S. PATENT DOCUMENTS 7,241,807 B2 * 7/2007 Xu et al. .................. 514/512

FOREIGN PATENT DOCUMENTS

| CN | 1744908 | | 3/2006 |
| CN | 1744908 A | * | 3/2006 |
| CN | 101885735 | | 11/2010 |

OTHER PUBLICATIONS

Zaragoza Dorwald, Side Reactions in Organic Synthesis, 2005, Wiley-VCH Verlag GmbH & Co. KGaA, Weinheim, Preface. p. IX.*

* cited by examiner

*Primary Examiner* — Paul A Zucker
(74) *Attorney, Agent, or Firm* — Cesari and McKenna LLP

(57) ABSTRACT

Hydroxy acid compound of substituted phenyl ester, preparation method and medical use thereof are provided. The title compound is shown in formula (I), $Y=C_{1-4}$ straight carbon chain. The compound can release 2,6-diisopropylphenol rapidly under the action of enzymes in vivo, which has sedative, hypnotic and/or anesthetic effect. By protecting the hydroxyl group of 2, 6-diisopropylphenol in compound of formula (I), the first-pass metabolic activity of 2, 6-diisopropylphenol is reduced, so that the synthetic compound can be used for sedation, hypnosis, and/or anesthesia.

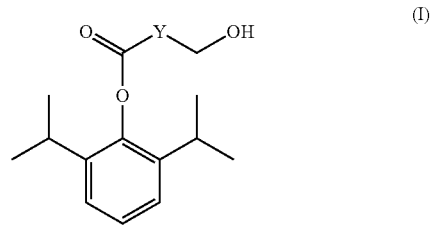

16 Claims, 2 Drawing Sheets

HYDROXY ACID ESTER COMPOUND OF SUBSTITUTED PHENOL, PREPARATION METHOD AND MEDICAL USE THEREOF

CROSS-REFERENCE TO RELATED APPLICATIONS

This application is the National Stage of International Application No. PCT/CN2010/001600, filed on Oct. 13, 2010, which claims priority of Chinese Application No. 20101206936.1, filed Jun. 23, 2010. The contents of both applications are hereby incorporated by reference in their entirety.

FIELD OF THE INVENTION

The present invention relates to a hydroxy acid ester compound of substituted phenol, preparation method and medical use thereof The compound can be used as a sedative-hypnotic agent and/or anesthetic administered intravenously or non-intravenously.

BACKGROUND OF THE INVENTION

Propofol (chemical name: 2,6-diisopropylphenol) is a sedative-hypnotic agent that has been widely used in clinical practice for induction and maintenance of general anesthesia and for intensive care. Propofol has the characteristics of rapid onset and fast metabolic inactivation, and so it has increasingly been used widely in the world since its first clinical report in 1977. As the water solubility of propofol is only 146 mg/L, its clinical formulation is an oil-in-water (O/W) emulsion, in which propofol accounts for 1%; soybean oil, 10%; glycerol, 2.25%; and purified egg yolk lecithin, 1.2%. In the U.S.A, for example, 0.005% disodium edetate is also included as a bacteria growth inhibitor. This formula is a milk-white liquid with a pH value of 7.0, which is slightly viscous, easily injectable, stable at room temperature, and insensitive to light, and is packed in ampoules, under nitrogen gas. However, this preparation still has many disadvantages. For example, as an emulsion form for injection, various stabilizers and solubilizers contained can inevitably cause allergic reactions. Soybean oil and lecithin contained can breed bacteria easily; therefore, it must be prepared under the strict aseptic condition, and it is hard to store when unsealed. Meanwhile, a big oil droplet contained may cause embolism or even serious cardiac adverse effects. Besides, this kind of formulation cannot overcome the disadvantage of 2,6-diisopropylphenol being easily oxidized and deteriorated. All of these disadvantages have limited the use of 2,6-diisopropylphenol to some extent.

Some chemical methods have been reported to overcome those disadvantages of 2,6-diisopropylphenol, which inevitably involved the preparation of some water-soluble prodrugs by modification of the hydroxyl group of 2,6-diisopropylphenol, such as propofol phosphates disclosed in WO200213810. But some of those compounds could not rapidly release 2,6-diisopropylphenol in vivo and could not achieve a rapid induction of anesthesia. For another example, the prodrugs disclosed in WO2003059255 could release formaldehyde molecules after hydrolysis, which could cause some adverse effects. For one more example, the propofol succinic acid monoester sodium salt disclosed in WO200213810 is a derivative of 2,6-diisopropylphenol with high water-solubility, but it is unstable in aqueous solution, which also limits the development and application of water-soluble prodrugs of 2,6-diisopropylphenol.

SUMMARY OF THE INVENTION

In view of the above problems, the present invention provides a hydroxy acid ester compound of substituted phenol for the first time; the present invention also provides a preparation method and a medical use of the compound.

The hydroxy acid ester compound of substituted phenol of the present invention is represented by the following structure formula (I):

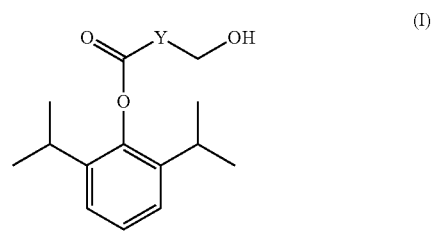

wherein, Y is $C_{1-4}$ straight carbon chain; preferably, the straight carbon chain Y is a saturated carbon chain; more preferably, the straight carbon chain Y is —$CH_2$—$CH_2$— or —$CH_2$—$CH_2$—$CH_2$—.

Besides the simple straight carbon chain forms, the straight carbon chain Y in the compound of the above formula (I) may also be the substituted forms where at least one hydrogen atom of the carbon chain may be substituted with a member of the group consisting of methyl, ethyl, cyclopropyl, hydroxy, sulfydryl, amino or substituted amino group.

The experimental results have shown that as a propofol prodrug, the inventive compound of formula (I) can rapidly decompose and release the substituted phenol structure (propofol) to produce sedative, hypnotic and/or anesthetic effect when it is formulated into a pharmaceutically acceptable dosage form, e.g., emulsion administered intravenously in vivo; therefore, the weakness of the hydroxyl group being easily oxidized in the substituted phenol structure can be prevented, and the compound exhibits the advantages of being stable in vitro and being rapidly decomposed in vivo. Meanwhile, the hydroxy acid or its corresponding esterified products that are released from the compound of formula (I) are harmless in vivo. Accordingly, when administered intravenously or non-intravenously as a central depressant to produce sedative, hypnotic and/or anesthetic effect on animals or human beings, the hydroxy acid ester compound of substituted phenol of formula (I) of the present invention can have desirable actions and effects. The hydroxyl group of the compound of formula (I) can be further modified to obtain some other derivatives that have a higher stability. For example, when the hydroxyl group is bound to the water-soluble molecules, various water-soluble derivatives of the substituted phenol can be obtained based on the above-mentioned structure.

The above hydroxy acid ester compound of substituted phenol can be prepared by the following steps: reacting 2,6-diisopropylphenol (II) as a raw material with dicarboxylic anhydride compound (III) in the presence of a deacidifying agent and 4-dimethylaminopyridine as a catalyst, to form diacid monoester intermediate (IV); or reacting 2,6-diisopropylphenol (II) with diacid compound (III') in the presence of N,N-dicyclohexylcarbodiimide (DCC) as a condensating agent and a catalytic amount of 4-dimethylaminopyridine, to form diacid monoester intermediate (IV); then diacid monoester intermediate (IV) with sodium borohydride and iodine, to obtain the corresponding hydroxy acid ester compound of substituted phenol (I). Wherein, Y of said dicarboxylic anhydride compound (III) and diacid compound (III') is C$_{1-4}$ straight carbon chain. The reaction routes are as follows:

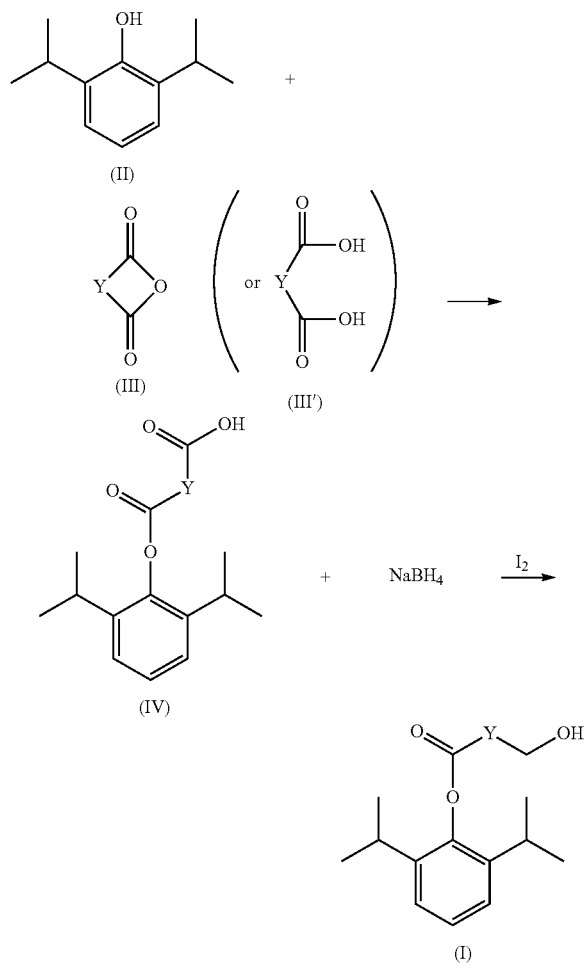

In the reaction route, Y of diacid compound (III') or dicarboxylic anhydride compound (III) is a saturated carbon chain and, preferably, is —CH$_2$—CH$_2$— or —CH$_2$—CH$_2$—CH$_2$—.

Said deacidifying agent in the above preparation method may be an organic alkaline compound, e.g., pyridine or a tertiary amine compound such as triethylamine Said preparation method can usually be performed in at least one organic solvent selected from the group consisting of methylene dichloride, chloroform, carbon tetrachloride, chlorobenzene, benzene, methylbenzene, petroleum ether, cyclohexane, n-hexane, acetonitrile, acetone, dimethylformamide (DMF), dimethyl sulphoxide (DMSO), tetrahydrofuran, diethyl ether, triethylamine or pyridine.

Typically, the compound of formula (I) of the present invention can be prepared by the following steps:

1': 2,6-diisopropylphenol (II) is dissolved in triethylamine, added with dianhydride compound (III) and a catalytic amount of 4-dimethylaminopyridine. After completion of the reaction under stirring, triethylamine is removed under reduced pressure. Experiment results show that the reaction can be performed at the temperatures ranging from room temperature to reflux temperature, or even a lower temperature below 0° C. After the removal of triethylamine, the residue is added with water and adjusted with a conventional acid, e.g., hydrochloric acid, until an acidic pH point is reached so that the precipitate is formed completely. The precipitate is separated to obtain diacid monoester intermediate of 2,6-diisopropylphenol (IV). Besides dianhydride compound (III), 2,6-diisopropylphenol can also be allowed to react with an equimolar amount of diacid compound (III') under the temperatures ranging from 0° C. to room temperature in the presence of an equimolar amount of N,N-dicyclohexylcarbodiimide (DCC) as a condensating agent and a catalytic amount of 4-dimethylaminopyridine. After completion of the reaction, the reactant is filtered to remove the precipitate and the filtrate is evaporated to remove the solvent to obtain diacid monoester intermediate (IV). The resultant crude diacid monoester intermediate (IV) may be further recrystallized with cyclohexane/ethyl acetate, or other suitable solvents to obtain the purified intermediate (IV).

2'. Diacid monoester intermediate (IV) obtained from the above step is mixed with an equimolar amount of sodium borohydride in the above-mentioned organic solvent (e.g., anhydrous tetrahydrofuran), and added with an equimolar amount of iodine under stirring. After completion of the reaction (e.g., no bubbles occurring, the reaction solution turning to colorless), the reaction solution is evaporated under reduced pressure to remove tetrahydrofuran, and the residue is dissolved with said organic solvent (e.g., ethyl acetate) and washed with water sufficiently; then, the organic solvent is removed to obtain the target product of formula (I) as a colorless transparent viscous liquid.

It could be understood that by preparing the hydroxy acid ester derivative of 2,6-diisopropylphenol (propofol), the hydroxy acid ester compound of substituted phenol of formula (I) of the present invention can overcome the weakness of easy oxidization of the hydroxyl group in the propofol structure, exhibit its advantages of being stable in vitro and being rapidly decomposed in vivo, and thus it can be used in a central depressant drug to produce sedative, hypnotic and/or anesthetic effect on animals or human beings through an intravenous or non-intravenous route, so that the application scope of the propofol prodrugs can be enlarged.

The present invention will be further described in detail in conjunction with the embodiments shown in the drawings and examples; however, it should not be construed as limiting the scope of the present invention to the following examples. Without departing from the technical thought of the present invention, various modifications or changes can be made in accordance with the ordinary skills and the conventional means in the field and should be included in the scope of the present invention.

DETAILED DESCRIPTION OF THE INVENTION

Example 1

Figure 1:
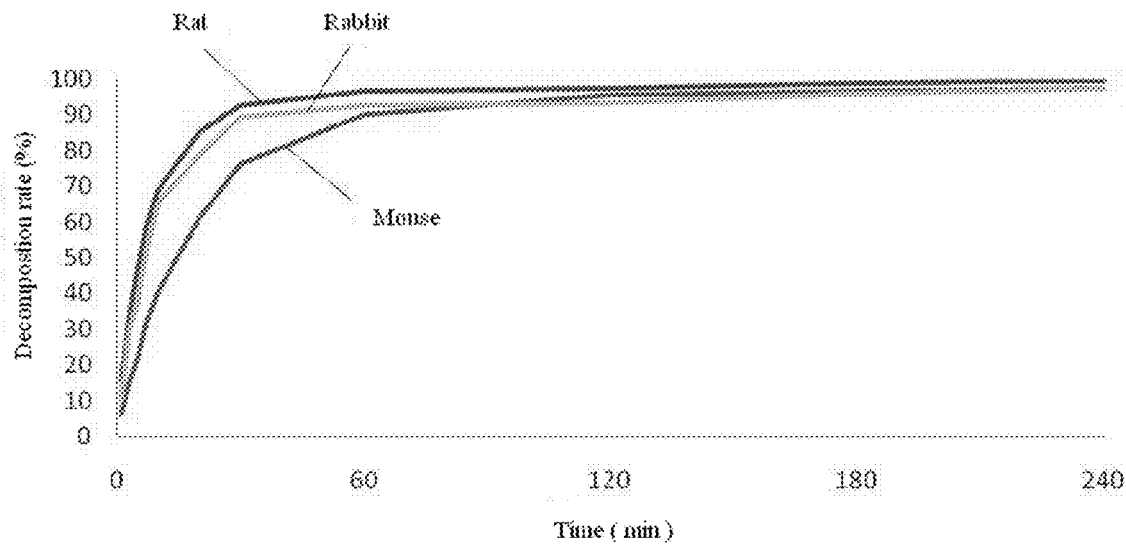
FIG. 1 is an in vitro decomposition curve of propofol hydroxybutyrate in the plasma.

20 g of 2,6-diisopropylphenol (propofol) was dissolved in 50 ml of triethylamine, added with 14 g of succinyl oxide and 0.02 g of DMAP (4-dimethylamino-pyridine).The mixture was reacted completely for 16 hours under stirring at room temperature, and the reaction solution was evaporated under reduced pressure to remove triethylamine The residue was added into 100 ml of water and adjusted to pH 1 with 6N HCl to produce a great amount of white precipitate. The precipitate was separated and then dried under reduced pressure to give crude propofol succinate monoester intermediate, which was recrystallized with cyclohexane/ethyl acetate to obtain 23.5 g of acicular crystals. Yield: 75.4%, mp: 103-104° C.

2.54 g of sodium tetrahydroborate was suspended in 45 ml of anhydrous tetrahydrofuran, cooled to below 5° C., and then slowly added dropwise with 18 g of propofol succinic acid monoester intermediate in 60 ml of tetrahydrofuran, with the temperature maintaining below 5° C. After completion of the dropwise addition, the mixture was stirred at this low temperature for 2 hours until no bubbles occurred, and then added dropwise with 8.28 g of iodine in 70 ml of tetrahydrofuran, with the color of the solution not becoming yellow. After completion of the dropwise addition, the mixture was stirred for 1 hour under the constant temperature. The reaction solution was evaporated to remove tetrahydrofuran, and added with 100 ml of ethyl acetate to produce precipitate. The precipitate was filtered off and the filtrate was washed once with 100 ml of saturated sodium bicarbonate solution and 100 ml of water, respectively. The organic layer was separated, dried over anhydrous magnesium sulfate, and then evaporated to remove ethyl acetate solvent to obtain 16.24 g of propofol ω-hydroxybutyrate product as colorless oil. No impurity was detected by TLC. Yield: 95%.

Structure Detection:

1) NMR spectrometer: BRUKER 400M, using $CDCl_3$ as a solvent and TMS as an internal standard. δ was expressed in ppm.
$^1$HNMR (δ): 1.19-1.20 (2s, 12H), 1.62 (s, 1H), 2.04-2.06 (m, 4H), 2.76-2.79 (m, 2H), 2.89-2.91 (m, 2H), 3.78-3.800 (m, 2H), 7.15-7.26 (m, 3H). Wherein, the peak at 1.62 (s, 1H) was the signal of active hydrogen of the hydroxyl group.

2) NMR spectrometer: BRUKER 400M, using $CDCl_3$ as a solvent and TMS as an internal standard. δ was expressed in ppm.
$^{13}$CNMR (δ): 22.71, 22.76, 23.67, 27.55, 27.69, 30.77, 61.96, 123.93, 126.53, 140.29, 145.51, 172.57. Wherein, the signal of carbon atom bonded to the hydroxyl group was shown at 61.96, and the signal of carbonyl carbon of the ester bond was shown at 173.57.

3) High-resolution mass spectrometric detection: Mass Spectrometer: API 3000 LC-Ms/Ms (ABI, U.S.A.); Ionization Mode: EDI.
Ms+: 265.1808 ($C_{16}H_{25}O_3$).

Example 2

20 g of propofol was dissolved in 100 ml of methylene dichloride, added with 13.3 g of succinic acid, 0.02 g of dimethylaminopyridine, and then 23.2 g of DCC. The mixture was reacted for 6 hours under stirring at room temperature, then the reaction solution was filtered to remove white solid and the filtrate was washed once with 150 ml of 6N HCl. The organic layer was separated and evaporated under reduced pressure to remove the solvent to give crude propofol succinate monoester intermediate as pale yellow solid, which was recrystallized with cyclohexane/ethyl acetate to obtain 26.6 g of white acicular crystals. Yield: 85%, mp: 102-103° C.

The method of preparing the final product propofol w-hydroxybutyrate (I) from propofol succinate monoester intermediate was similar to that of Example 1.

Example 3

10 g of propofol was dissolved in 50 ml of triethylamine, added with 7 g of glutaric anhydride and 0.01 g of DMAP. The mixture was stirred for 12 hours under stirring at room temperature, and the reaction solution was evaporated under reduced pressure to remove excessive triethylamine The residue was added into 100 ml of water and adjusted to pH 1 with 6N HCl to produce a great amount of white precipitate. The precipitate was separated and then dried under reduced pressure to give crude propofol glutarate monoester intermediate, which was recrystallized with cyclohexane/ethyl acetate to obtain 10.8 g of white flaky crystals. Yield: 65.9%, mp: 53-54° C.

2.54 g of sodium tetrahydroborate was suspended in 45 ml of anhydrous tetrahydrofuran, cooled to below 5° C., and then slowly added dropwise with 19 g of propofol glutarate monoester intermediate in 60 ml of tetrahydrofuran, with the temperature maintaining below 5° C. After completion of the dropwise addition, the mixture was stirred at low temperature for 2 hours until no bubbles occurred, and then added dropwise with 8.28 g of iodine in 70 ml of tetrahydrofuran, with the color of the solution not becoming yellow. After completion of the dropwise addition, the mixture was stirred for 1 hour under the constant temperature. The reaction solution was evaporated to remove tetrahydrofuran, and added with 100 ml of ethyl acetate to produce precipitate. The precipitate was filtered off and the filtrate was washed once with 100 ml of saturated sodium bicarbonate solution and 100 ml of water, respectively. The organic layer was separated, dried over anhydrous magnesium sulfate, filtered to remove the drying agent and then evaporated to remove ethyl acetate to obtain 16.24 g of propofol ω-hydroxyvalerate product as colorless oil. No impurity was detected by TLC. Yield: 93%.

Structure Detection:

1) NMR spectrometer: BRUKER 400M, using $CDCl_3$ as a solvent and TMS as an internal standard. δ was expressed in ppm.
$^1$HNMR(δ): 1.19-1.20 (2s, 12H), 1.71-1.73 (m, 2H), 1.88-1.91 (m, 2H), 2.67-2.69 (m, 2H), 2.87-2.91 (m, 2H), 3.71-3.73(m, 2H), 7.15-7.26 (m, 3H).

2) NMR spectrometer: BRUKER 400M, using $CDCl_3$ as a solvent and TMS as an internal standard. δ was expressed in ppm.
$^{13}$CNMR(δ): 14.19, 21.05, 21.15, 27.55, 32.10, 33.73, 62.18, 123.90, 126.48, 140.27, 145.52, 172.33. Wherein, the signal of carbon atom bonded to the hydroxyl group was shown at 62.18, and the signal of carbonyl carbon of the ester bond was shown at 172.33.

3) High-resolution mass spectrometric detection: Mass Spectrometer: API 3000 LC-Ms/Ms (ABI, U.S.A.); Ionization Mode: EDI.
Ms$^+$: 279.1959 ($C_{17}H_{26}O_3$)

Example 4

10 g of propofol was dissolved in 50 ml of methylene dichloride, added with 7.4 g of glutaric acid, 0.01 g of DMAP, and then 11.6 g of DCC. The mixture was reacted for 6 hours under stirring at room temperature, then the reaction solution was filtered to remove white solid and the filtrate was washed once with 80 ml of 6N HCl. The organic layer was separated and evaporated under reduced pressure to remove the solvent to give pale yellow solid, which was recrystallized with cyclohexane/ethyl acetate to obtain 9 g of propofol glutarate monoester intermediate as white acicular crystals. Yield: 54.9%, mp: 53-54° C.

The method of preparing the final product propofol w-hydroxyvalerate (I) from propofol glutarate monoester intermediate was similar to that of Example 3.

Example 5

In vitro Decomposition Test of Propofol Hydroxybutyrate in the Plasma

Three parallel solutions of propofol hydroxybutyrate of Example 1 with a concentration of 10 mg/ml were prepared, added into and mixed with the mouse, rat or rabbit plasma, which was pre-placed in water bath (37° C.), respectively. 100 μl of the drug-containing plasma was taken at 0 min, 1 min, 3 min, 5 min, 7 min, 10 min, 20 min, 30 min, 1 h, 2 h, 3 h and 4 h, respectively, and the concentrations of the active metabolite propofol were determined by the HPLC method. The results have shown that propofol hydroxybutyrate in the plasma can be rapidly decomposed into the active compound propofol. An in vitro decomposition rate curve of propofol hydroxybutyrate in the plasma is shown in FIG. 1.

Example 6

In vitro Decomposition Test of Propofol Hydroxyvalerate in the Plasma

Figure 2:
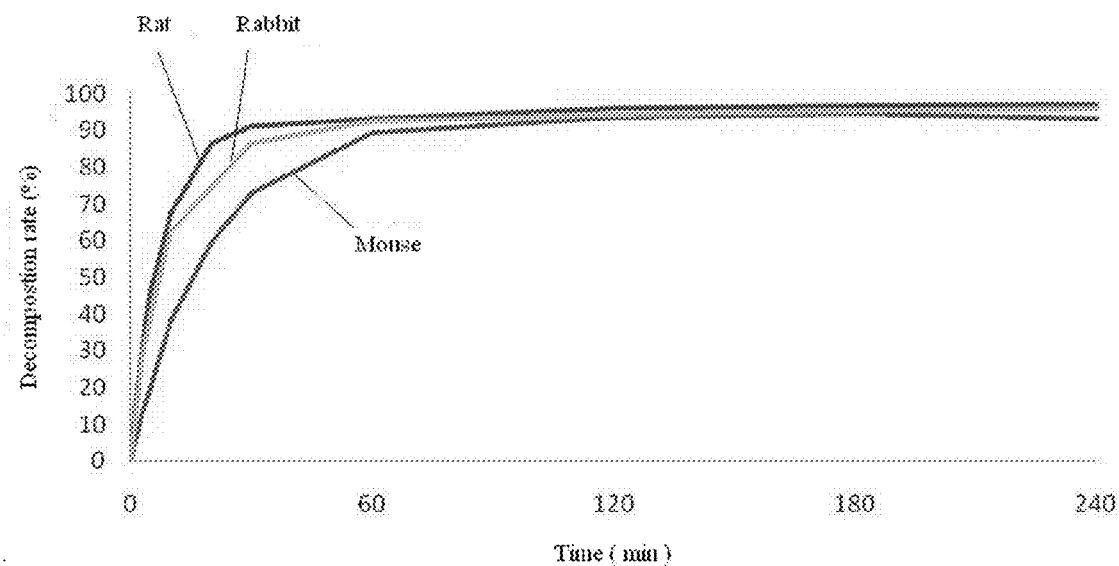
FIG. 2 is an in vitro decomposition curve of propofol hydroxyvalerate in the plasma.
Figure 3:
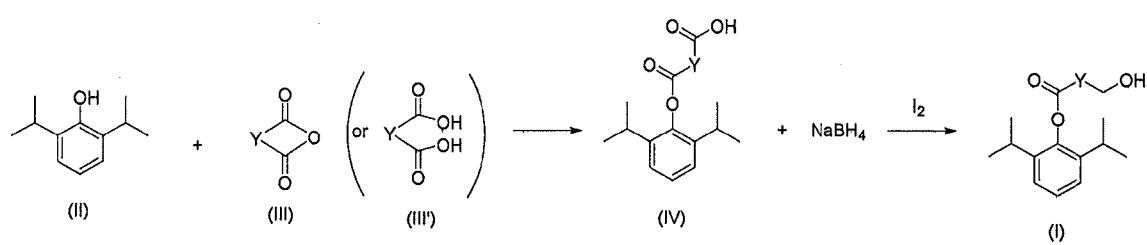
FIG. 3 is a general synthetic route for preparing a hydroxyl acid ester compound of substituted phenol.

Three parallel solutions of propofol hydroxyvalerate of Example 3 with a concentration of 10 mg/ml were prepared, added into and mixed with mouse, rat or rabbit plasma, which was pre-placed in water bath (37° C.), respectively. 100 μl of the drug-containing plasma was taken at 0 min, 1 min, 3 min, 5 min, 7 min, 10 min, 20 min, 30 min, 1 h, 2 h, 3 h and 4 h, respectively, and the concentrations of the active metabolite propofol were determined by the HPLC method. The results have shown that propofol hydroxyvalerate in the plasma can be rapidly decomposed into the active compound propofol. An in vitro decomposition rate curve of propofol hydroxyvalerate in the plasma is shown in FIG. 2.

Example 7

Preliminary Pharmacodynamic Test of Propofol Hydroxybutyrate

60 Kunming mice with half males and half females were randomly divided into the drug test group (propofol hydroxybutyrate of the present invention) (n=30) and the Diprivan™ control group (positive control drug Diprivan™) (n=30). Median effective doses ($ED_{50}$) of the substituted phenol hydroxy acid ester and Diprivan™ were determined by the up-and-down method. In the test, the mice were injected with the drugs through the tail veins, with the disappearance of the forepaw righting reflex (FRR) of the mice as a judgment index of the end point of anesthesia; the recovery of FRR of the mice as an index of recovery from anesthesia. The results showed that $ED_{50}$ of the drug test group of the present invention was 52 mg/kg, with the 95% confidence interval of 35~67 mg/kg. $ED_{50}$ of the Diprivan™ control group was 6.1 mg/kg, with 95% confidence interval of 5.1~7.9 mg/kg. During the determination of $ED_{50}$, it was observed that the disappearance time of FRR of the drug test group of the present invention was 45.3±12.3 seconds, and the recovery time was 235.6±67.9 seconds. Both the onset time and the recovery time were slightly longer than those of the Diprivan™ control group (onset time, 19±3 seconds; recovery time, 217.6±67.3 seconds). The test results have shown that propofol hydroxybutyrate of the present invention has a definite and reversible anesthetic effect.

Example 8

Preliminary Pharmacodynamic Test of Propofol Hydroxyvalerate

60 Kunming mice with half males and half females were randomly divided into the drug test group (propofol hydroxyvalerate of the present invention) (n=30) and the Diprivan™ control group (positive control drug Diprivan™) (n=30). Median effective doses ($ED_{50}$) of the substituted phenol hydroxy acid ester and Diprivan™ were determined by the up-and-down method. In the test, the mice were injected with the drugs through the tail veins, with the disappearance of FRR of the mice as a judgment index of the end point of anesthesia; the recovery of FRR of the mice as an index of recovery from anesthesia. The results showed that $ED_{50}$ of the drug test group of the present invention was 60 mg/kg, with 95% confidence interval of 36~72 mg/kg. $ED_{50}$ of the Diprivan™ control group was 6.5 mg/kg, with 95% confidence interval of 4.9~8.1 mg/kg. During the determination of $ED_{50}$, it was observed that the disappearance time of FRR of the drug test group of the present invention was 46.1±9.5 seconds, and the recovery time was 256.1±61.2 seconds. Both the onset time and the recovery time were slightly longer than those of the Diprivan™ control group (onset time, 21±4 seconds; recovery time, 210.4±56.6 seconds). The test results have shown that propofol hydroxybutyrate of the present invention has a definite and reversible anesthetic effect.

INDUSTRIAL APPLICABILITY

The present invention provides a hydroxy acid ester derivative of 2,6-diisopropylphenol (propofol). The compound of the present invention overcomes the disadvantage of the hydroxyl group being easily oxidized in the structure of propofol, and it has the characteristics of being stable in vitro and being rapidly decomposed in vivo; thus, it can be used as a central depressant to produce sedative, hypnotic and/or anesthetic effect on animals or human beings through an intravenous or non-intravenous route, so that the application scope of the propofol prodrug can be enlarged and the positive sense and good prospects can be achieved. So, it is suitable for the industrial applications.

What is claimed is:

1. A hydroxy acid ester compound of substituted phenol represented by the following structure formula (I):

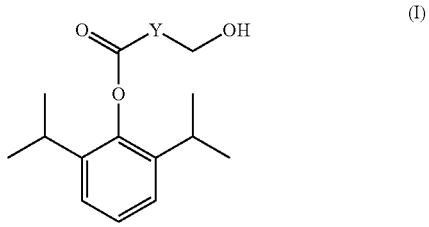

wherein Y is a straight saturated carbon chain of —CH$_2$—CH$_2$or —CH$_2$—CH$_2$—CH$_2$—, the straight saturated carbon chain optionally substituted with methyl, ethyl, cyclopropyl, hydroxy, sulfhydryl, amino, or a substituted amino group.

2. The compound of claim 1, wherein said straight carbon chain Y is —CH$_2$—CH$_2$or —CH$_2$—CH$_2$—CH$_2$—.

3. The compound of claim 1, wherein the straight saturated carbon chain is substituted with methyl, ethyl, cyclopropyl, hydroxy, sulfhydryl, amino, or a substituted amino group.

4. A method of preparing the hydroxy acid ester compound of substituted phenol of claim 1, comprising the steps of:
reacting 2, 6-diisopropylphenol (II) as a raw material with a dicarboxylic anhydride compound (III) in the presence of a deacidifying agent and 4-dimethylaminopyridine as a catalyst to form a diacid monoester intermediate (IV); or, alternatively, reacting 2, 6-diisopropylphenol (II) with a diacid compound (III') in the presence of N, N-dicyclohexylcarbodiimide as a condensating agent and a catalytic amount of 4-dimethylaminopyridine to form a diacid monoester intermediate (IV); and then reacting the diacid monoester intermediate (IV) with sodium borohydride and iodine, to obtain the hydroxy acid ester compound of substituted phenol (I); wherein said dicarboxylic anhydride compound (III) is

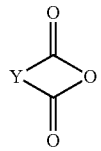

and said diacid compound (III') is

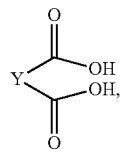

in which Y is a straight saturated carbon chain of —CH$_2$—CH$_2$— or —CH$_2$—CH$_2$—CH$_2$—, the straight saturated carbon chain optionally substituted with methyl, ethyl, cyclopropyl, hydroxy, sulfhydryl, amino, or a substituted amino group.

5. The preparation method of claim 4, wherein said deacidifying agent is pyridine or a tertiary amine compound.

6. The preparation method of claim 4, wherein said preparation method is performed in at least one organic solvent selected from the group consisting of methylene dichloride, chloroform, carbon tetrachloride, chlorobenzene, benzene, methylbenzene, petroleum ether, cyclohexane, n-hexane, acetonitrile, acetone, DMF, DMSO, tetrahydrofuran, diethyl ether, triethylamine and pyridine.

7. The preparation method of claim 6, wherein the steps are conducted by:

dissolving 2, 6-diisopropylphenol (II) in triethylamine, adding said dicarboxylic anhydride compound (III) and a catalytic amount of 4-dimethylaminopyridine, completing the reaction under stirring, removing the triethylamine under reduced pressure, adding water and then an acid to adjust the pH of the residue to be acidic to produce a precipitate; separating out the precipitate to obtain a diacid monoester intermediate of said 2, 6-diisopropylphenol (IV); or, alternatively, reacting 2, 6-diisopropylphenol (II) as a raw material with an equimolar amount of said diacid compound (III') completely at the temperatures ranging from 0° C. to room temperature in the presence of an equimolar amount of N, N-dicyclohexylcarbodiimide as a condensating agent and a catalytic amount of 4-dimethylaminopyridine, filtering the reaction solution, and evaporating the resulting filtrate to remove the solvent to obtain the diacid monoester intermediate (IV); and mixing the diacid monoester intermediate (IV) obtained from the above step with an equimolar amount of sodium borohydride in anhydrous tetrahydrofuran, adding an equimolar amount of iodine under stirring, reacting the resulting mixture completely, evaporating the reaction solution under reduced pressure to remove tetrahydrofuran, dissolving the residue in an organic solvent and washing the organic solution with water, and removing the organic solvent to obtain the target product of formula (I) as a colorless transparent viscous liquid.

8. The preparation method of claim 7, wherein Y of said diacid compound (III') or dicarboxylic anhydride compound (III) is —CH$_2$—CH$_2$— or —CH$_2$—CH$_2$—CH$_2$—.

9. A method for producing a sedative effect, a hypnotic effect, and/or an anesthetic effect comprising administering to a subject in need thereof an effective amount of the hydroxy acid ester compound of substituted phenol of claim 1 through an intravenous or non-intravenous route.

10. A method of preparing the hydroxy acid ester compound of substituted phenol of claim 2, comprising the steps of:

reacting 2, 6-diisopropylphenol (II) as a raw material with a dicarboxylic anhydride compound (III) in the presence of a deacidifying agent and 4-dimethylaminopyridine as a catalyst to form a diacid monoester intermediate (IV); or, alternatively, reacting 2, 6-diisopropylphenol (II) with a diacid compound (III') in the presence of N, N-dicyclohexylcarbodiimide as a condensating agent and a catalytic amount of 4-dimethylaminopyridine to form a diacid monoester intermediate (IV); and then reacting the diacid monoester intermediate (IV) with sodium borohydride and iodine, to obtain the hydroxy acid ester compound of substituted phenol (I); wherein said dicarboxylic anhydride compound (III) is

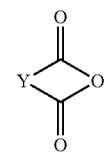

and said diacid compound (III') is

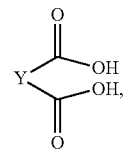

in which Y is a straight saturated carbon chain of —CH$_2$—CH$_2$— or —CH$_2$—CH$_2$—CH$_2$—, the straight saturated carbon chain optionally substituted with methyl, ethyl, cyclopropyl, hydroxy, sulfhydryl, amino, or a substituted amino group.

11. A method of preparing the hydroxy acid ester compound of substituted phenol of claim 3, comprising the steps of:

reacting 2, 6-diisopropylphenol (II) as a raw material with a dicarboxylic anhydride compound (III) in the presence of a deacidifying agent and 4-dimethylaminopyridine as a catalyst to form a diacid monoester intermediate (IV); or, alternatively, reacting 2, 6-diisopropylphenol (II) with a diacid compound (III') in the presence of N, N-dicyclohexylcarbodiimide as a condensating agent and a catalytic amount of 4-dimethylaminopyridine to form a diacid monoester intermediate (IV); and then reacting the diacid monoester intermediate (IV) with sodium borohydride and iodine, to obtain the hydroxy acid ester compound of substituted phenol (I); wherein said dicarboxylic anhydride compound (III) is

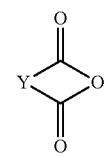

and said diacid compound (III') is

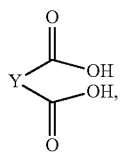

in which Y is a straight saturated carbon chain of —CH$_2$—CH$_2$— or —CH$_2$—CH$_2$—CH$_2$—, the straight saturated carbon chain optionally substituted with methyl, ethyl, cyclopropyl, hydroxy, sulfhydryl, amino, or a substituted amino group.

12. The preparation method of claim 10, wherein said deacidifying agent is pyridine or a tertiary amine compound.

13. The preparation method of claim 11, wherein said deacidifying agent is pyridine or a tertiary amine compound.

14. The preparation method of claim 5, wherein said deacidifying agent is pyridine or triethylamine.

15. The preparation method of claim 12, wherein said deacidifying agent is pyridine or triethylamine.

16. The preparation method of claim 13, wherein said deacidifying agent is pyridine or triethylamine.

* * * * *